United States Patent
McLaughlin et al.

(10) Patent No.: US 11,559,287 B2
(45) Date of Patent: Jan. 24, 2023

(54) TRANSDUCER SPECTRAL NORMALIZATION

(71) Applicant: Shenzhen Mindray Bio-Medical Electronics Co., Ltd., Shenzhen (CN)

(72) Inventors: Glen W. McLaughlin, San Carlos, CA (US); Albert Gee, Los Altos, CA (US)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 383 days.

(21) Appl. No.: 16/157,948

(22) Filed: Oct. 11, 2018

(65) Prior Publication Data

US 2020/0113549 A1    Apr. 16, 2020

(51) Int. Cl.
*A61B 8/14* (2006.01)
*G06T 5/10* (2006.01)
(Continued)

(52) U.S. Cl.
CPC .............. *A61B 8/58* (2013.01); *A61B 8/0825* (2013.01); *A61B 8/14* (2013.01); *G06T 5/10* (2013.01);
(Continued)

(58) Field of Classification Search
CPC ........... A61B 8/0825; A61B 8/14; A61B 8/58; G01S 7/52033; G01S 7/52047; G01S 7/52077; G06T 2207/10028; G06T 2207/10132; G06T 2207/20024; G06T 2207/20056; G06T 2207/30068; G06T 5/10
See application file for complete search history.

(56) References Cited

U.S. PATENT DOCUMENTS 4,561,019 A * 12/1985 Lizzi ................... G01S 7/52046
455/306
5,579,768 A * 12/1996 Klesenski ........... G01S 7/52033
600/442

(Continued)

FOREIGN PATENT DOCUMENTS

JP    2010246640 A  * 11/2010  ......... G01S 15/8959
JP    2010246640 A    11/2010
(Continued)

OTHER PUBLICATIONS

Espacenet translation of JP2010246640A (generated Mar. 18, 2021) (Year: 2010).*

(Continued)

*Primary Examiner* — Joseph M Santos Rodriguez
*Assistant Examiner* — Maria Christina Talty
(74) *Attorney, Agent, or Firm* — Kory D. Christensen (57) ABSTRACT

Systems and methods are disclosed for an ultrasound system. In various embodiments, a system is configured to receive echo data corresponding to a detection of an echo of a pulse signal, generate a set of transformations based on the echo data, and generate a set of point estimates for a frequency dependent filtering coefficient of a spectral response. The system is further configured to extract a set of attenuation coefficients based on the set of point estimates for the frequency dependent filtering coefficient and generate image data for the material of interest based on the set of attenuation coefficients.

10 Claims, 7 Drawing Sheets

(51) Int. Cl.
*A61B 8/00* (2006.01)
*A61B 8/08* (2006.01)

(52) U.S. Cl.
CPC ............... *G06T 2207/10028* (2013.01); *G06T 2207/10132* (2013.01); *G06T 2207/20024* (2013.01); *G06T 2207/20056* (2013.01); *G06T 2207/30068* (2013.01)

(56) References Cited

U.S. PATENT DOCUMENTS

| | | | | |
|---|---|---|---|---|
| 5,902,242 | A * | 5/1999 | Ustuner | G01S 15/8918 600/443 |
| 6,248,071 | B1 * | 6/2001 | Lin | G01S 7/52023 600/443 |
| 2005/0215896 | A1 * | 9/2005 | McMorrow | G06T 7/62 600/437 |
| 2008/0221449 | A1 * | 9/2008 | Sato | G01S 15/8988 600/442 |
| 2015/0029821 | A1 * | 1/2015 | Miyaki | G01S 7/52036 367/7 |
| 2016/0157814 | A1 * | 6/2016 | Palanisamy | A61B 8/4483 600/454 |
| 2016/0157828 | A1 * | 6/2016 | Sumi | G01N 29/262 702/189 |
| 2016/0262729 | A1 * | 9/2016 | Srinivasan | G01S 7/52085 |
| 2017/0007211 | A1 * | 1/2017 | Ichikawa | A61B 8/5269 |
| 2017/0112475 | A1 * | 4/2017 | Miyaki | A61B 8/5207 |

FOREIGN PATENT DOCUMENTS

| | | | | |
|---|---|---|---|---|
| JP | 5642910 | B1 * | 12/2014 | ........... A61B 8/5207 |
| JP | 5642910 | B1 | 12/2014 | |

OTHER PUBLICATIONS

Ali Sadeghi-Naini et al., "Low-frequency quantitative ultrasound imaging of cell death in vivo," Aug. 2013, Medical Physics, vol. 40, pp. 082901-1 through 082901-13 (Year: 2013).*

P. He and J.F. Greenleaf, "Attenuation Estimation on Phantoms—A Stability Test," 1986, Ultrasonic Imaging, 8, pp. 1-9 (Year: 1986).*

* cited by examiner

TRANSDUCER SPECTRAL NORMALIZATION

TECHNICAL FIELD

This disclosure relates to imaging systems and, in particular, to improving the performance and accuracy of ultrasound systems.

BACKGROUND OF THE INVENTION

Ultrasound imaging is a widely used for examining a wide range of materials and objects across a wide array of different applications. Ultrasound imaging provides a fast and easy tool for analyzing materials and objects in a non-invasive manner. As a result, ultrasound imaging is especially common in the practice of medicine as an ailment diagnosis, treatment, and prevention tool. Specifically, because of its relatively non-invasive nature, low cost and fast response time ultrasound imaging is widely used throughout the medical industry to diagnose and prevent ailments. Further, as ultrasound imaging is based on non-ionizing radiation it does not carry the same risks as other diagnosis imaging tools, such as X-ray imaging or other types of imaging systems that use ionizing radiation.

Ultrasound imaging is accomplished by generating and directing ultrasonic sound waves into a material of interest, first in a transmit phase and subsequently in a receive phase. During the transmit phase, an ultrasonic signal is transmitted into a material of interest by applying continuous or pulsed electronic signals. During the receive phase, reflections generated by boundaries between dissimilar materials are received by receiving devices, such as transducers, and converted to electrical signals. Signals can then be processed to determine the locations of the echo sources. The resulting data can be used to display images of inside a material of interest, e.g. by displaying images using a display device, such as a monitor.

Ultrasound imaging can offer a wealth of clinical information. Specifically, ultrasound imaging can be used in abdominal ultrasound (to visualize abdominal tissues and organs), bone sonometry (to assess bone fragility), breast ultrasound (to visualize breast tissue), Doppler fetal heart rate monitors (to listen to a fetal heart beat), Doppler ultrasound (to visualize blood flow through a blood vessel, organs, or other structures), echocardiogram (to view a heart), fetal ultrasound (to view a fetus in pregnancy), ultrasound-guided biopsies (to collect a sample of tissue), ophthalmic ultrasound (to visualize ocular structures) and ultrasound-guided needle placement (in blood vessels or other tissues of interest). Ultrasound imaging has also been used in describing various disease states, such as diseases of the liver, breast, prostate, thyroid or other organs through single measurements of stiffness or shear wave velocity.

SUMMARY

According to various embodiments, an ultrasound system includes a transducer and an image processor. The transducer is configured to transmit a first pulse signal into a tissue, receive an echo signal corresponding to the first pulse signal, and generate echo data based on the echo signal. The image processor is configured to generate a set of fast Fourier transforms based on the echo data, wherein each fast Fourier transform in the set of fast Fourier transforms is associated with a depth value. The image processor further generates a set of point estimates for a frequency dependent filtering coefficient of a spectral response, extract a set of attenuation coefficients based on the set of point estimates for the frequency dependent filtering coefficient, and compensate for spectral response reduction of the transducer based on the set of attenuation coefficients. In some embodiments, each point estimate in the set of point estimates corresponds to a fast Fourier transform in the set of fast Fourier transforms,

DETAILED DESCRIPTION

Ultrasound transducers typically have a limited bandwidth and spectral response variability. Certain aspects of the transducer technology may be improved by using single crystal transducers, composite material transducers, capacitive micromachined ultrasonic transducers (CMUTs), piezoelectric micromachined ultrasonic transducers (PMUTs), or other improvements. As a result, there is a large variety of transducer types, each with different characteristics, performance, and shortcomings. However, there is still a great need for further improving ultrasound performance. Aspects of the subject technology provide for techniques and systems for measuring and shaping a spectral response, which results in an increased spectral bandwidth. Furthermore, the subject technology provides a robust solution that can be applied to a wide variety of different transducer types and is compatible with other improvements in transducer technology.

The properties of a medium that the ultrasonic pulse travels through (e.g., the material of interest, such as organic tissue) may also affect the ultrasonic echo and distorts the resulting ultrasound image. For example, the medium may have an attenuation property and, in many cases, the attenuation property may be dependent on frequency. In other words, the medium may attenuate lower frequency ultrasonic signals (or the lower frequency portions of an ultrasonic signal) less than higher frequency ultrasonic signals (or the higher frequency portions of the ultrasonic signal). Furthermore, the rates at which ultrasonic signals are attenuated may vary based on the properties of the medium such as composition, density, layers, location of objects in the medium, etc. This may be especially true when the medium is organic tissue that may include a number of layers and/or components that may each have different characteristics. Furthermore, these layers and/or components may be dispersed throughout the tissue in a non-uniform manner.

Aspects of the subject technology also provide for techniques and systems that compensate for the frequency dependent attenuation property of the medium and how the property affects attenuation at different depths.

Some aspects of the subject technology relate to processes, systems, and/or instructions stored on machine-readable medium that provide technical solutions to the above technical problems and others. For example, according to some embodiments, a transducer may be configured to transmit a pulse signal into a tissue. The pulse signal may be a broad spectrum long time coded calibration pulse, for example a chirp, (as opposed to an imaging pulse of short time but broad spectrum). Ultrasound echoes are generated based on reflections of the transmitted pulse signal on boundaries, objects, or other components in the tissue at various depths. These echoes may be received by the transducer and translated into echo data.

A set of fast Fourier transforms may be generated based on the received echo data. Each fast Fourier transform in the set may be associated with a particular depth value or range of depths. These depth values and ranges may be disjoint or, in some cases, overlap. A point estimates for a frequency dependent filtering coefficient of a spectral response for the each fast Fourier transform may also be generated. These point estimates may be used to form a line. In some cases, normalization steps may also be taken to smooth out the line. For example, a least means square fit process may be used.

A set of attenuation coefficients may be extracted from the line formed by the point estimates and these attenuation coefficients may be used to compensate for spectral response limitations of the transducer or for frequency dependent attenuation of the tissue of interest. For example, a second pulse signal may be transmitted into the tissue. This second pulse, in some cases, may be an imaging pulse that is shorter in time but still has a broad bandwidth than the initial calibration pulse used above. Echo data for the second pulse signal may be received and used, along with the set of attenuation coefficients, to generate an image of the tissue. For example, the attenuation coefficients may be used as inverse filters for the image data.

Although some embodiments may be discussed with respect to organic tissues, other mediums, materials, or objects of interest may similarly be used. Furthermore, although fast Fourier transforms are discussed with respect to some embodiments, other algorithms or signal conversion methods may also be used.

Various aspects of certain embodiments may be implemented using hardware, software, firmware, or a combination thereof. As used herein, a software module or component may include any type of computer instruction or computer executable code located within or on a computer-readable storage medium. A software module may, for instance, comprise one or more physical or logical blocks of computer instructions, which may be organized as a routine, program, object, component, data structure, etc., that performs one or more tasks or implements particular abstract data types.

In certain embodiments, a particular software module may comprise disparate instructions stored in different locations of a computer-readable storage medium, which together implement the described functionality of the module. Indeed, a module may comprise a single instruction or many instructions, and may be distributed over several different code segments, among different programs, and across several computer-readable storage media. Some embodiments may be practiced in a distributed computing environment where tasks are performed by a remote processing device linked through a communications network.

The embodiments of the disclosure will be best understood by reference to the drawings, wherein like parts are designated by like numerals throughout. The components of the disclosed embodiments, as generally described and illustrated in the figures herein, could be arranged and designed in a wide variety of different configurations. Furthermore, the features, structures, and operations associated with one embodiment may be applicable to or combined with the features, structures, or operations described in conjunction with another embodiment. In other instances, well-known structures, materials, or operations are not shown or described in detail to avoid obscuring aspects of this disclosure.

Thus, the following detailed description of the embodiments of the systems and methods of the disclosure is not intended to limit the scope of the disclosure, as claimed, but is merely representative of possible embodiments. In addition, the steps of a method do not necessarily need to be executed in any specific order, or even sequentially, nor need the steps be executed only once.

Figure 1:
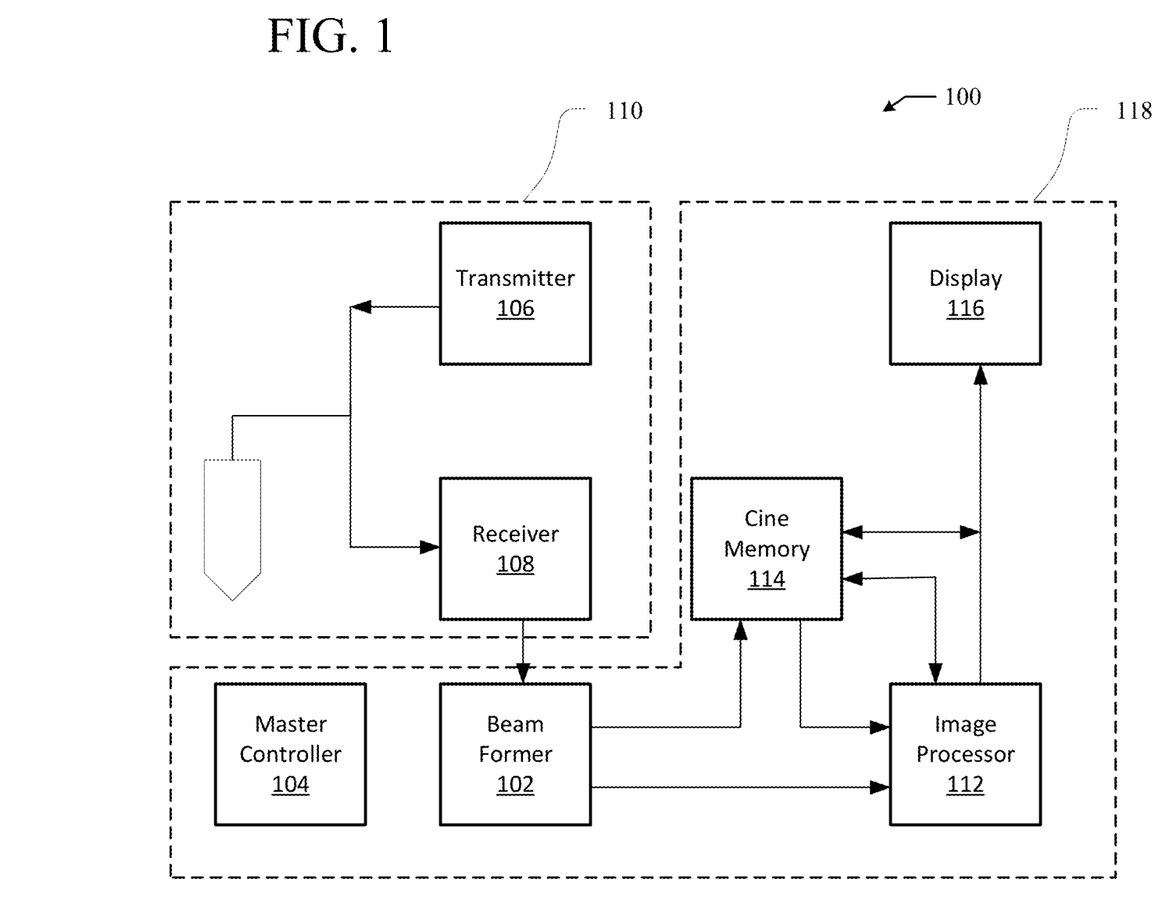
FIG. 1 illustrates an example of an ultrasound system.

FIG. 1 illustrates an example of an ultrasound system 100. The ultrasound system 100 shown in FIG. 1 is merely an example system and in various embodiments, the ultrasound system 100 can have less components or additional components. Specifically, the ultrasound system 100 can be an ultrasound system where the receive array focusing unit is referred to as a beam former 102, and image formation can be performed on a scanline-by-scanline basis. System control can be centered in the master controller 104, which accepts operator inputs through an operator interface and in turn controls the various subsystems. For each scan line, the transmitter 106 generates a radio-frequency (RF) excitation voltage pulse waveform and applies it with appropriate timing across the transmit aperture (defined by a sub-array of active elements) to generate a focused acoustic beam along the scan line. RF echoes received by the receive aperture 108 of the transducer 110 are amplified and filtered by the receiver 108, and then fed into the beam former 102, whose function is to perform dynamic receive focusing; i.e., to re-align the RF signals that originate from the same locations along various scan lines.

The image processor 112 can perform processing specific to active imaging mode(s) including 2D scan conversion that transforms the image data from an acoustic line grid to an X-Y pixel image for display. For Spectral Doppler mode, the image processor 112 can perform wall filtering followed by spectral analysis of Doppler-shifted signal samples using typically a sliding FFT-window. The image processor 112 can also generate the stereo audio signal output corresponding to forward and reverse flow signals. In cooperation with the master controller 104, the image processor 112 also can format images from two or more active imaging modes, including display annotation, graphics overlays and replay of cine loops and recorded timeline data.

The cine memory 114 provides resident digital image storage for single image or multiple image loop review, and acts as a buffer for transfer of images to digital archival devices. On most systems, the video images at the end of the data processing path can be stored to the cine memory. In state-of-the-art systems, amplitude-detected, beam formed data may also be stored in cine memory 114. For spectral Doppler, wall-filtered, baseband Doppler I/Q data for a user-selected range gate can be stored in cine memory 114. Subsequently, the display 116 can display ultrasound images created by the image processor 112 and/or images using data stored in the cine memory 114.

The beam former 102, the master controller 104, the image processor, the cine memory 114, and the display can be included as part of a main processing console 118 of the ultrasound system 100. In various embodiments, the main processing console 118 can include more or fewer components or subsystems. The ultrasound transducer 110 can be incorporated in an apparatus that is separate from the man processing console 118, in a separate apparatus that is wired or wirelessly connected to the main processing console 118. This allows for easier manipulation of the ultrasound transducer 110 when performing specific ultrasound procedures on a patient.

Figure 2:
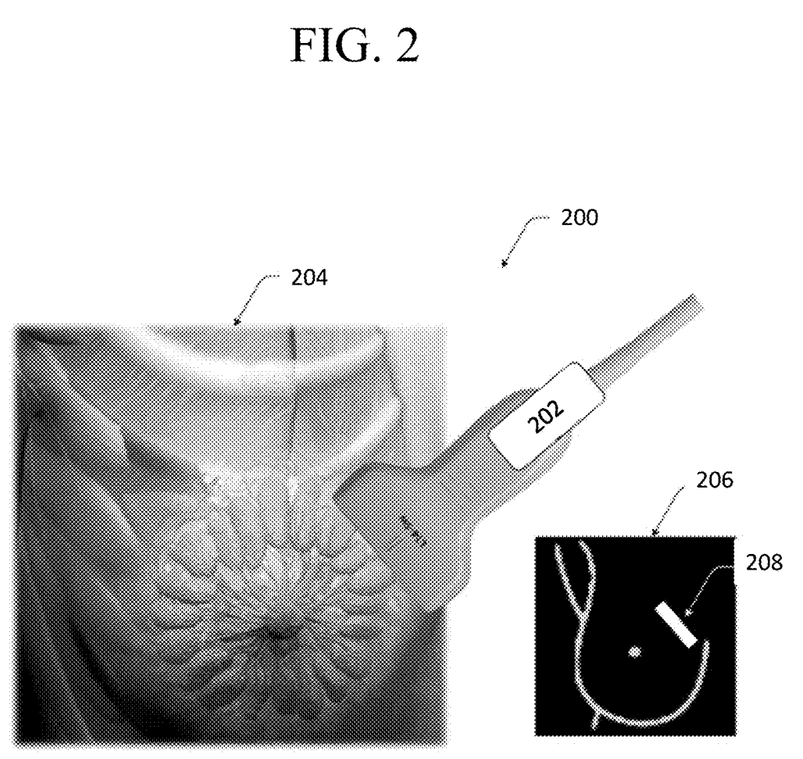
FIG. 2 illustrates an example system for controlling a main processing console of an ultrasound system.

FIG. 2 illustrates an example system 200 for controlling a main processing console of an ultrasound system. The main processing console can be an applicable main processing console for processing ultrasound image data in an ultrasound system, such as the main processing console 118 show in the example system 100 in FIG. 1. The system 200 is shown with respect to scanning of a breast. Specifically, the system 200 includes a linear transducer/ultrasound transducer 202 with respect to a breast for purposes of scanning the breast is shown in FIG. 2. A sketch of the anatomy of a breast is shown in 204. The linear transducer 202 is in contact with the breast in the upper left region of the right breast. This position is self-annotated in the body marker image of the right breast, 206, with the linear transducer position/orientation indicator, 208.

Ultrasound control functions include applicable functionalities for controlling a main processing console of an ultrasound system, e.g. remote from the main processing console of the ultrasound system. Specifically ultrasound control functions can include applicable functions that a user can provide input for to control a main processing console in gathering, processing, and reproducing ultrasound images as part of an ultrasound procedure.

An ultrasound control function can include a freeze control function. For example, an ultrasound control function can include a control for freezing a display at a specific ultrasound image. Additionally, an ultrasound control function can include a depth control function for changing a depth of field or focus for gathering ultrasound image data. Further, an ultrasound control function can include a gain control for adjusting amplification of received/reflected signals for ultrasound images. An ultrasound control function can also include a storage control for controlling how data of ultrasound image data is stored and subsequently processed to reproduce ultrasound images. Further, an ultrasound control function can include an auto-optimization control for enabling automatic optimization of either or both a gain and an overall contrast in an ultrasound image. Additionally, an ultrasound control function can include a set reference control for specifying and selecting a reference frame for ultrasound imaging. An ultrasound control function can also include a start clip control to control creation of an ultrasound clip. Further, an ultrasound control function can include a change mode control for controlling an image mode used to gather and process ultrasound images in an ultrasound procedure. Additionally, an ultrasound control function can include a move region of interest control that is used to adjust a region of interest in a medium scanned during an ultrasound procedure. An ultrasound control function can also include a biopsy guide control for adjusting presentation of a biopsy guide in an ultrasound procedure. Further, an ultrasound control function can include a body marker select control for selecting a body marker image used in an ultrasound procedure.

Although the system 200 is shown with respect to scanning of a breast using a linear transducer/ultrasound transducer 202, other types of tissues, mediums, or materials of interest may be scanned using other types of transducers and/or ultrasound systems.

As noted above, ultrasound systems operate on a limited bandwidth and/or have a limited reliable spectral response. The properties of the medium (e.g., the tissue) that the ultrasound system is directed at also distort ultrasound signals and, as a result, distort any resulting ultrasound image. Various embodiments of the subject technology are directed to improving these and other technical issues with ultrasound technology.

According to various embodiments, spectral measurements of the signals at various depths can be made and an estimate of the frequency dependent attenuation coefficient along with the passband response of the transducer can be obtained. Given that the attenuation coefficient of tissue will attenuate higher frequencies at a different rate (e.g., a faster rate) than lower frequencies the overall attenuation of the spectral response from the initial transmit spectral pulse is filtered into a lower and lower center frequency signal with narrower and narrower bandwidth as it propagates through the tissue. As the beams are formed the system can interrogate areas that represent primarily speckle so that a clean spectral estimate can be obtained at each depth.

According to some embodiments, the spectral estimates may be overlapping in depth to various extents. Several beam formed lines may also be used to get multiple spectral estimates and these estimates may be normalized or averaged to improve the overall signal to noise ratio (SNR) at each depth. Alternatively or additionally, the data may be averaged in place in a coherent manner to improve the overall SNR as well.

Once these spectral estimates are calculated at various depths, the known spectral characteristics of the transmit pulse along with the measured spectral estimates at depth can be used to estimate the transducer transfer function as well as the attenuation of properties of the tissues with depth. This information can then be used to generate depth dependent inverse filters to compensate to some extent to the narrowing bandwidth and rate of frequency downshift of the waveform as it propagates through the tissue resulting in improving the system detail resolution performance characteristics at depth. The system may further be configured to measure the spectral SNR at the various depths and automatically determine and adjust how much gain should be applied to the signals at various depths and/or frequencies to ensure that it is primarily signal being compensated instead of just the noise.

According to some embodiments, the image processing of the incoming data from the reflected transmit pulse may include forming an image based on the one or more processing algorithms. These image forming algorithms may include beam formation, synthetic aperture techniques, or adaptive image formation techniques. This data could be obtained with either a unique transmit pulse that is used to obtain a more comprehensive spectral bandwidth of the system and tissue or with a standard imaging pulse. In some embodiments, a first estimate based on a unique pulse for large adjustment may be generated and a standard transmit pulse may be used to generate subsequent estimates to track changes for fine adjustments. Once the image has been formed, a gain compensation may be applied based on previous measurements. If there have been no previous measurements than an initial estimate of the gain compensation may be calculated without compensation.

A moving block Fast Fourier Transform (FFT) in the range direction may be performed in accordance with various embodiments. These transforms may be generated with overlapping ranges so that a smooth estimate of the parameters and compensation required can be made. In other embodiments, the FFTs may not have any overlap in range. Several FFTs along different range lines can be used to improve the overall estimate as their spectral profile can be averaged or the system can also coherently average several transmit/receive cycles in place to improve the overall SNR of the signal. The transducer and system parameter compensation may be applied to the signals in the spectral domain so that a slope calculation of the attenuation coefficient can be calculated. In some embodiments, once there is an estimate of the attenuation coefficient is estimated on a point basis, a moving average and/or least means squares fit can be applied to get a smoother varying estimate of the tissue attenuation to be compensated for and the calculation of the range-based gain compensation can be updated.

One aspect of the present disclosure relates to a system. The system may include one or more hardware processors configured by machine-readable instructions. The processor(s) may be configured to receive echo data corresponding a detection of an echo of a pulse signal. The echo data may be associated with a variety of depths of a material of interest. The processor(s) may be configured to generate a set of transformations based on the echo data. Each transformation in the set of transformations may be associated with a depth value. The processor(s) may be configured to generate a set of point estimates for a frequency dependent filtering coefficient of a spectral response. Where each point estimate in the set of point estimates may correspond to a transformation in the set of transformations. The processor(s) may be configured to extract a set of attenuation coefficients based on the set of point estimates for the frequency dependent filtering coefficient. The processor(s) may be configured to generate image data for the material of interest based on the set of attenuation coefficients.

Another aspect of the present disclosure relates to a method. The method may include receiving echo data corresponding a detection of an echo of a pulse signal. The echo data may be associated with a variety of depths of a material of interest. The method may include generating a set of transformations based on the echo data. Each transformation in the set of transformations may be associated with a depth value. The method may include generating a set of point estimates for a frequency dependent filtering coefficient of a spectral response. Where each point estimate in the set of point estimates may correspond to a transformation in the set of transformations. The method may include extracting a set of attenuation coefficients based on the set of point estimates for the frequency dependent filtering coefficient. The method may include generating image data for the material of interest based on the set of attenuation coefficients.

Yet another aspect of the present disclosure relates to a non-transient computer-readable storage medium having instructions embodied thereon, the instructions being executable by one or more processors to perform a method. The method may include receiving echo data corresponding a detection of an echo of a pulse signal. The echo data may be associated with a variety of depths of a material of interest. The method may include generating a set of transformations based on the echo data. Each transformation in the set of transformations may be associated with a depth value. The method may include generating a set of point estimates for a frequency dependent filtering coefficient of a spectral response. Where each point estimate in the set of point estimates may correspond to a transformation in the set of transformations. The method may include extracting a set of attenuation coefficients based on the set of point estimates for the frequency dependent filtering coefficient. The method may include generating image data for the material of interest based on the set of attenuation coefficients.

Figure 3:
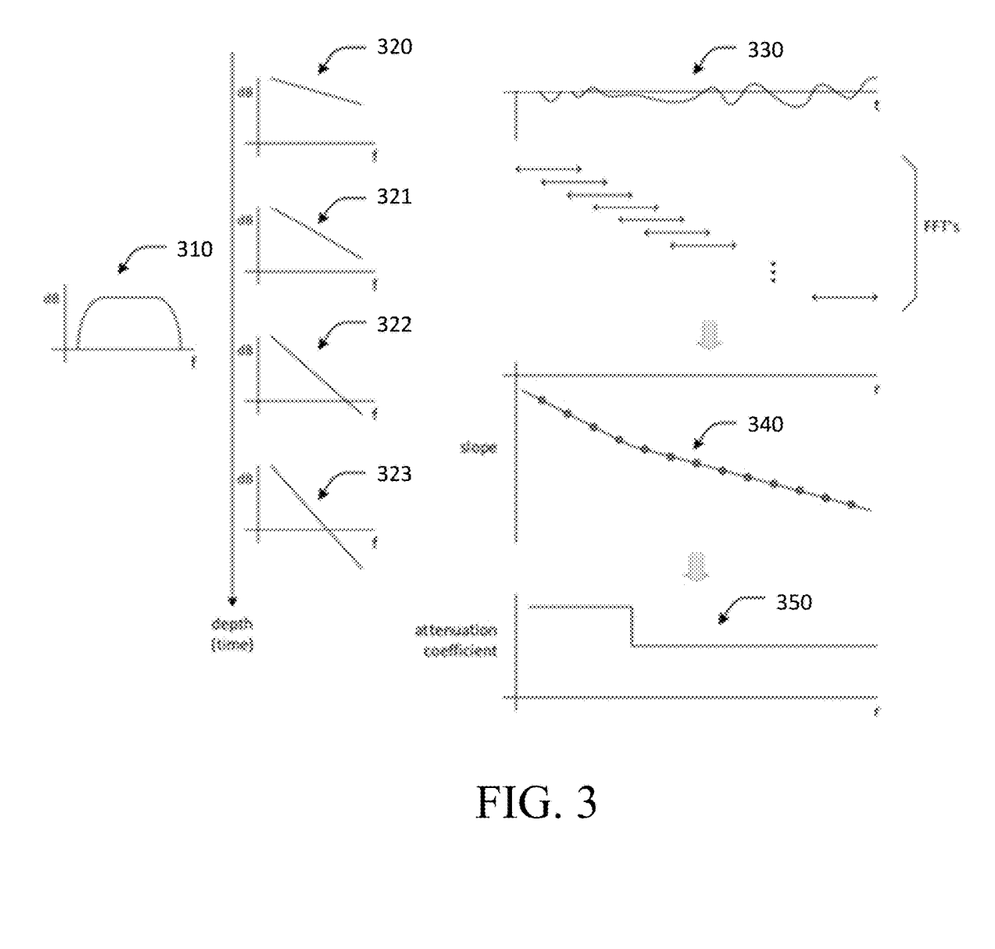
FIG. 3 is a diagram illustrating a process for generating a set of attenuation coefficients.

FIG. 3 is a diagram illustrating a process for generating a set of attenuation coefficients. In particular, FIG. 3 includes a graph 310 of a pulse signal. In particular, the graph 310 illustrates the amplitude (in decibels dB) and frequency of a pulse signal, such as a broad spectrum or broadband calibration pulse. According to various embodiments, a known broadband calibration pulse represented by graph 310 may be transmitted by the ultrasound system for a period of time into a tissue. Echoes caused by reflections and interactions between the broadband calibration pulse and the tissue at various depths may be received by the ultrasound system.

The calibration pulse may be filtered and distorted from interactions with both the transducer of the ultrasound system as well as the tissue. For example, in the near field, the distortion and filter effect may be primarily due to the transducer while, as the signal propagates through various depths, the spectral filtering of the higher frequencies increases. This is illustrated in graphs 320, 321, 322, and 323. More specifically, the graphs 320, 321, 322, and 323 help illustrate that different tissue depths (e.g., the time needed for ultrasound pulses to reach the tissue depth and echo), affect the spectral filtering of ultrasound pulses. The higher frequencies of the calibration pulse are filtered at a greater rate than the lower frequencies of the calibration pulse. Furthermore, as depth increases in graphs 320, 321, 322, and 323, this effect increases in prominence.

Based on the received signals from various scan lines at various depths (as illustrated in graphs 320, 321, 322, and 323), a set of overlapping in range fast Fourier transforms (FFTs) may be calculated. The set of FFTs is illustrated by graph 330. As illustrated by the graph 330, in some embodiments, the range of depths may overlap. In other embodiments, however, the depth values may not be ranges and/or may not overlap.

From this set of FFTs, point estimates of the slope of the line for the frequency dependent filtering coefficient of the spectral response can be calculated. These point estimates are illustrated by graph 340. From these point estimates a least means squares fit can be performed across a sub set of points to obtain an improved estimate of regional values of the slope of the line for the frequency dependent filtering of the spectral response. The regional slope of the frequency dependent filtering coefficient of the spectral response represents the corresponding attenuation coefficient. As a result, a set of attenuation coefficients may be extracted based on the set of point estimates. This is illustrated by graph 350, which shows 2 attenuation coefficients calculated for the portion of the line shown in graph 340. Conceptually, these attenuation coefficients may represent a change in slope in the line for the frequency dependent filtering coefficient in graph 340. These attenuation coefficients may be used to calculate a range dependent compensation filter to compensate for some of the spectral response reduction in the signal resulting in improved image performance from a detail resolution figure of merit measurement.

Various embodiments of the subject technology relate to obtaining an estimate of the depth varying spectral characteristics of the transmitted waveform. For example, a known transmit pulse spectrum may be transmitted and received at a range of depths of the tissue. The digitized signals may be processed in an image formation stage. A number of image formation techniques are possible to be used ranging from standard digital beam formation, synthetic aperture techniques, and adaptive image formation techniques. If there are already estimates for the gain compensation, those estimates may be applied. However, on a first iteration of the process (or if no estimate is available), the over depth gain compensation will most likely default to a standard value, for example an identity function.

After the gain compensation is done, the gain compensated signals can be used to form an image to be displayed to the systems user. Additionally, or alternatively, these same signals may also use to calculate a correction factor for the next iteration of the process. For example, the signals used for calculating the gain compensation and the correction factors may be used to calculate a set of spectral energy profiles (e.g., FFTs). These spectral energy profiles may be overlapping in range. These set of range based FFTs may be used to analyze the signals and determine if any additional transducer (XDR) or system compensation is required prior to calculating the spectral slope.

The spectral slope is calculated in range. In particular, estimates of the frequency dependent attenuation property of the material being imaged may be calculated. From these measurements an attenuation coefficient calculation is extracted at various depths. The attenuation coefficient at increasing depths is used to compensate the spectral properties of the image with increasing range provided there is sufficient SNR at the higher frequencies.

Figure 4:
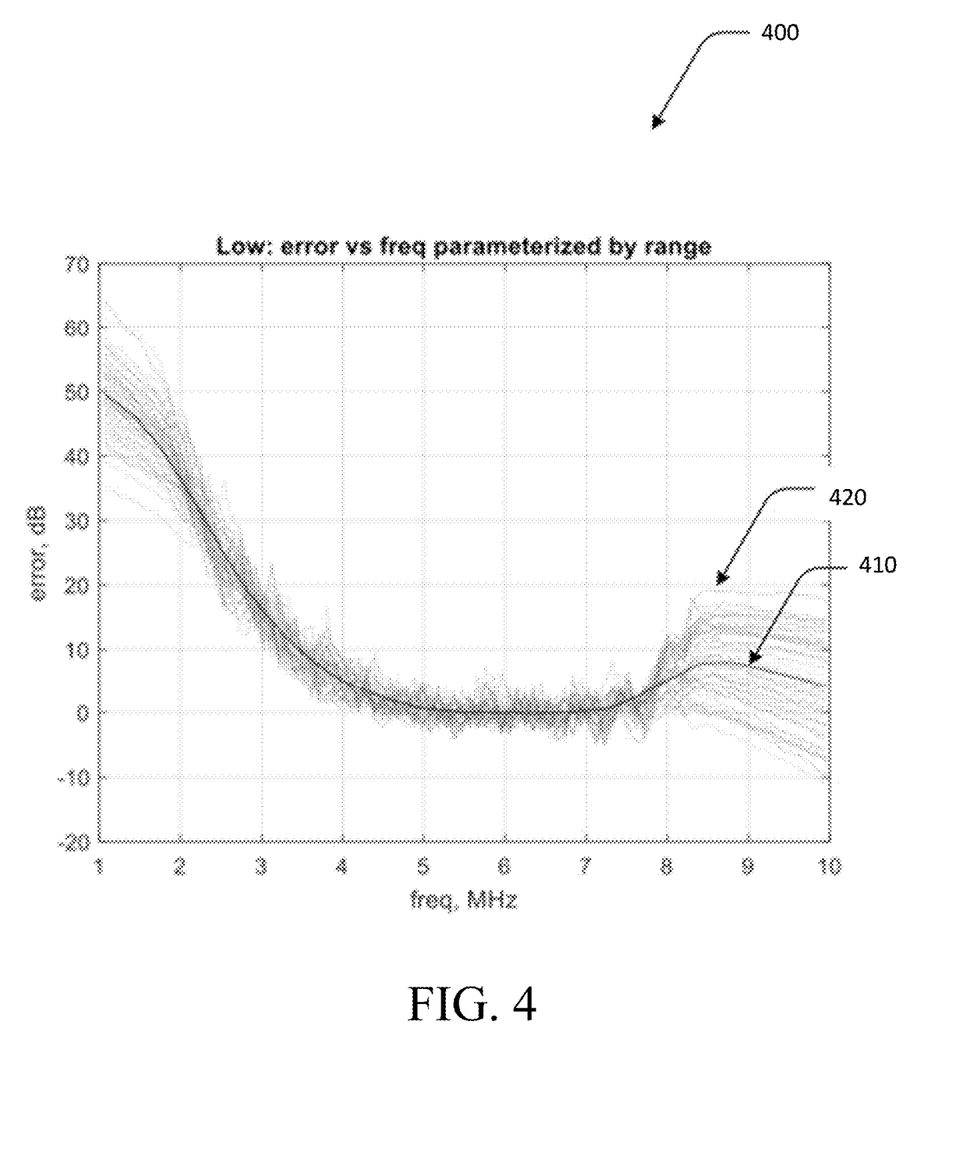
FIG. 4 is a graph illustrating a plot of the mean of the varying depth spectral estimates of a transducer, in accordance to various aspects of the subject technology.

FIG. 4 is a graph illustrating a plot 400 of the mean of the varying depth spectral estimates of a transducer, in accordance to various aspects of the subject technology. In particular, the mean estimate of the error of a flat spectral response of the transducer is show by the solid line 410. It should be noted that the transducer used to make these measurements was a linear transducer that had a spectral frequency range from about 3 MHz to 8 MHz. The spectral estimates of the transducer response for varying depths are shown by the dotted lines 420. From frequencies of about 2 MHz to about 8 MHz the variance of the individual depth varying spectral responses 420 is fairly constant around the mean spectral response 410. Above and below these frequencies the variance diverges quickly. The reason for the tighter variance at the lower frequencies is that the overall signal to noise is was higher as the medium that the signals were transmitted into attenuates higher frequency signals more than lower frequency signals so the signal to noise ratio (SNR) of the signal decrease as the frequency increases. As a result, various aspects of the subject technology enable a wider range of frequencies of a transducer to be useful and increases the accuracy and image resolution across the transducer.

Figure 5:
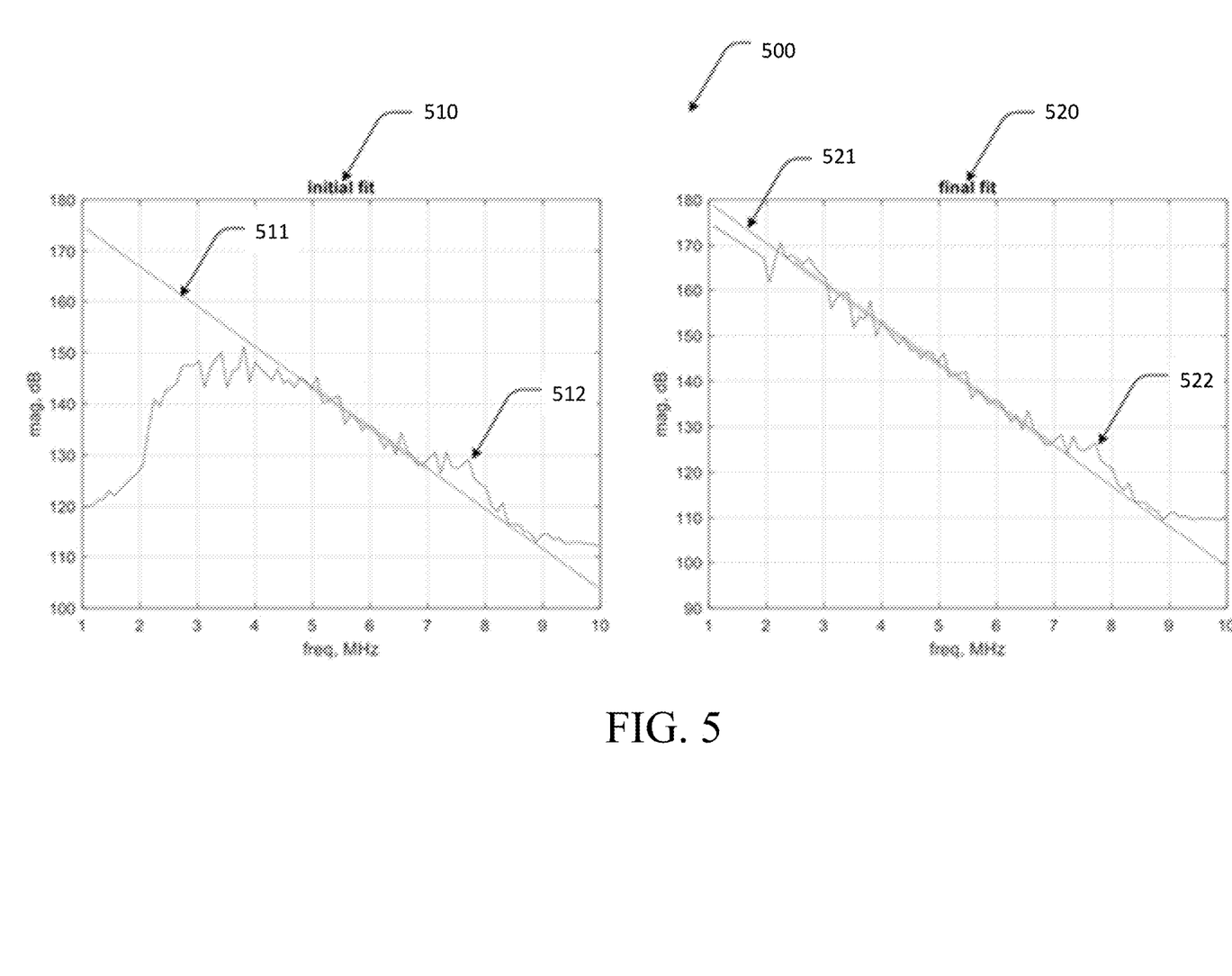
FIG. 5 is a set of graphs including a set of plots showing the spectral characteristics of a given depth from data uncompensated for transducer bandwidth limitation and one compensated.

FIG. 5 is a set of graphs 500 including a set of plots showing the spectral characteristics of a given depth from data uncompensated for transducer bandwidth limitation and one compensated. The uncompensated/raw spectral data in range is plotted in graph 510. The spectrum of this plot 512 of graph 510 shows a reasonably linear attenuation in dB with respect to frequency in the mid band of the transducer but the overall spectral fit to a line at the lower frequencies is minimal. A least mean squares fit line 511 using only the central portion of the spectrum for a given range of the uncompensated/raw spectral response is also shown in graph 510. As illustrated in graph 510, there is substantial roll off of the spectral signal at lower frequencies even though the overall SNR is good due to limitations of the transducer's frequency response characteristics.

A plot 522 of the compensated spectral data in range is plotted in graph 520. From this plot there is a significantly better linear attenuation in dB to frequency as compared to the uncompensated spectrum shown in graph 510. Also given the improved lower frequency spectral characteristics a least means squares fit line 521 is also improved. Comparing these two graphs 510 and 520 helps to illustrate that extracting the spectral response of the transducer and compensating for non-idealities in spectrum based on information contained within the spectral response of the transducer along a set of range samples is able to improve the overall systems spectral performance of various transducers and ultrasound systems.

Figure 6:
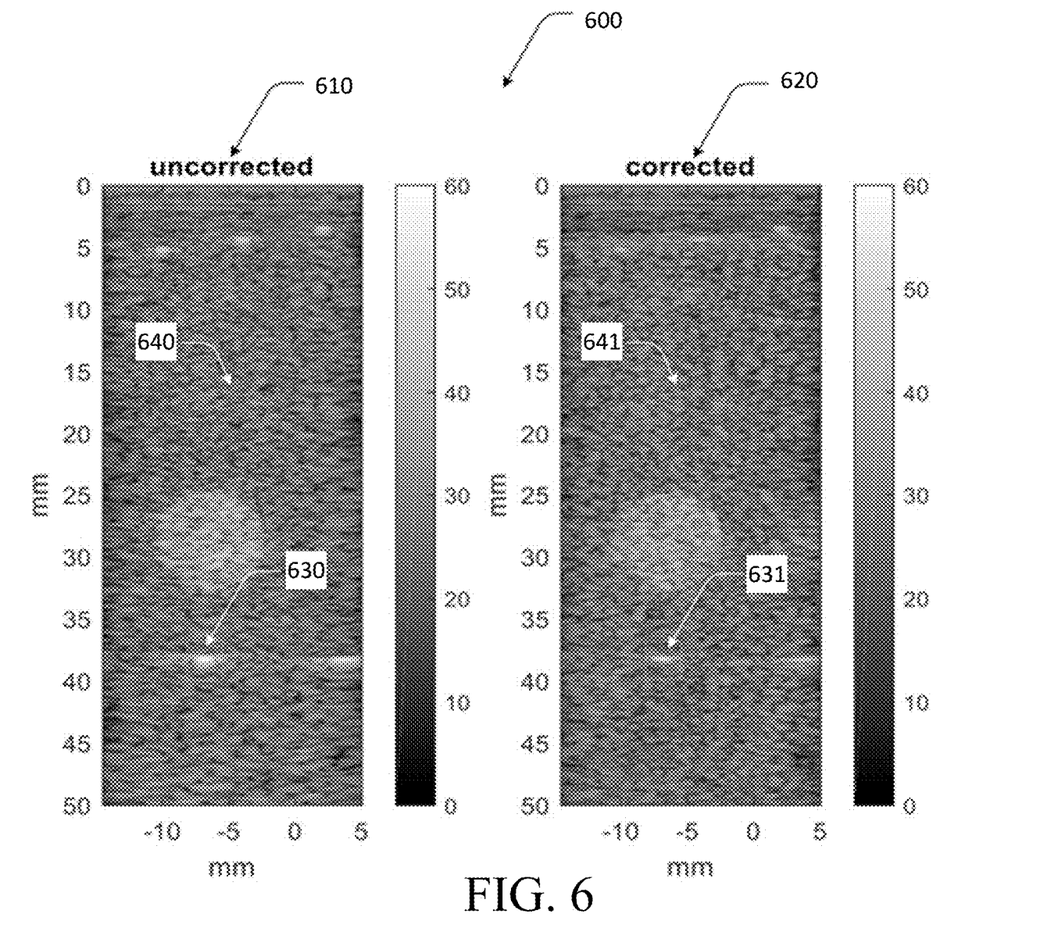
FIG. 6 shows a set of images based on data that is uncorrected and corrected for spectral broadening and transducer profile.

FIG. 6 shows a set of images 600 based on data that is uncorrected 610 and corrected 620 for spectral broadening and transducer profile. In the uncorrected image 610, the overall lower spectral bandwidth can be seen from a courser general speckle pattern 640 as well as lower axial resolution, as illustrated by point target 630. In the corrected image 620, a finer grain speckle pattern 641 is displayed as well as improved axial resolution, as illustrated by point target 631. It should be noted that both of these images were constructed with identical initial data and the uncorrected image 610 was processed through image formation methods while the corrected image 620 data was first processed to compensate for the spectral characteristics of the transducer as well as the attenuation of the tissue based on the technology described herein. After that processing it was then processed in the same image formation method as the uncorrected image 610. From these two images it is apparent that compensating for the transducer and tissue spectral characteristics results in an improved detail resolution image. An interesting item is to also note that the speckle pattern of the uncorrected 610 and the corrected 620 images are not highly correlated so that compounding of the two images can be done to get an image that has the nice detail resolution of the corrected image 620 but also improved contrast resolution.

Figure 7:
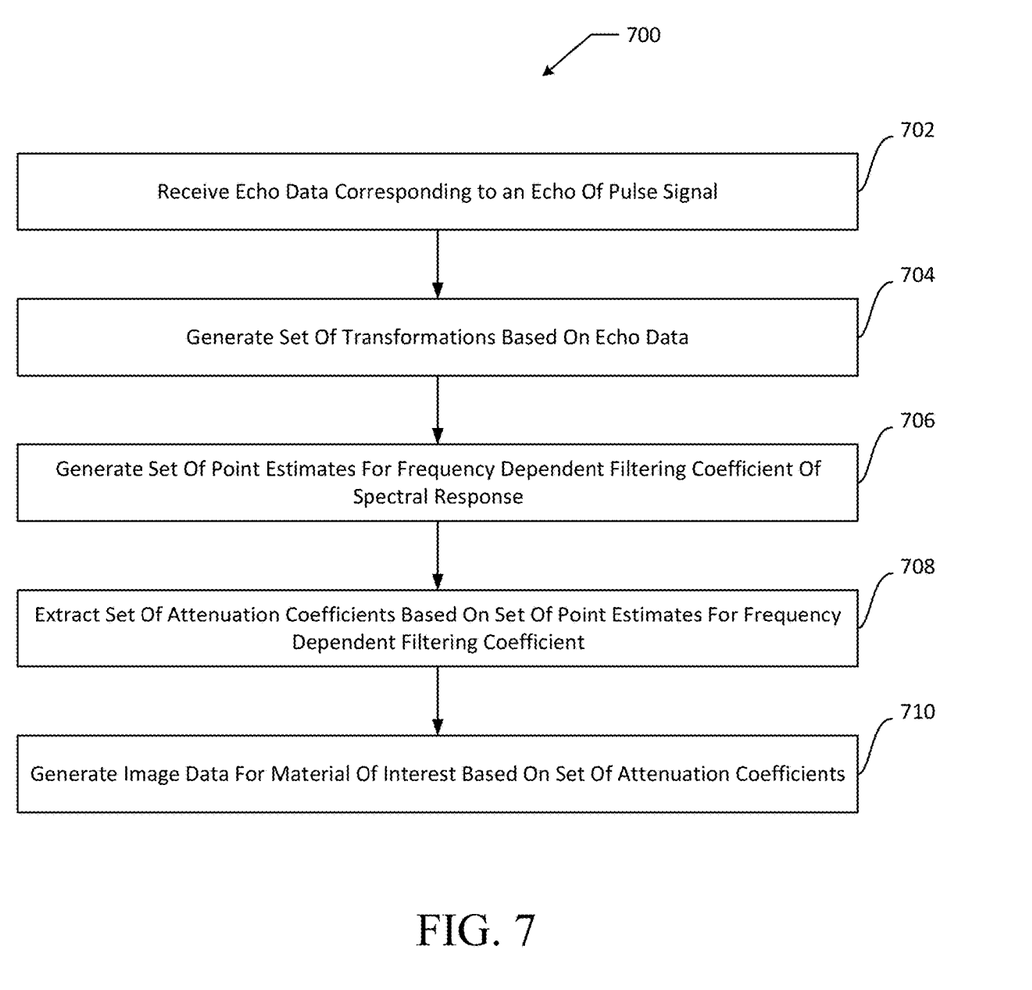
FIG. 7 is a flowchart illustrating an example method for generating image data for a material of interest, in accordance with various aspects of the subject technology.

FIG. 7 is a flowchart illustrating an example method 700 for generating image data for a material of interest, in accordance with various aspects of the subject technology. The operations of method 700 presented below are intended to be illustrative. In some implementations, method 700 may be accomplished with one or more additional operations not described, and/or without one or more of the operations discussed. Additionally, the order in which the operations of method 700 are illustrated in FIG. 7 and described below is not intended to be limiting.

In some implementations, method 700 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 700 in response to instructions stored electronically on an electronic storage medium. The one or more processing devices may include one or more devices configured through hardware, firmware, and/or software to be specifically designed for execution of one or more of the operations of method 700. For example, the method shown in FIG. 7 can be performed by an applicable ultrasound system, a transducer system, computing device, or similar system.

The system (e.g., the transducer component of an ultrasound system) may be configured to transmit a first pulse signal into a material of interest, such as organic tissue or other medium, receive echo signals corresponding to the first pulse signal, and generate echo data based on the echo signal. The first pulse signal may be, for example, a broad spectrum calibration pulse signal.

At operation 702, the system (e.g., an image processor component of the ultrasound system) may receive the echo data corresponding to the echo of a pulse signal. The echo data may be associated with a variety of depths of the material of interest. At operation 704, the system may generate a set of transformations based on the echo data. In some embodiments, the set of transformations may include one or more fast Fourier transforms (FFTs). However, other transformations or techniques may similarly be used. Each transformation in the set of transformations may be associated with a depth value. The depth values may be different ranges of depths corresponding to the variety of depths of the material of interest associated with the echo data. One or more of these depth values or ranges may also, in some embodiments, overlap.

At operation 706, the system (e.g., an image processor component of the ultrasound system) may generate a set of point estimates for a frequency dependent filtering coefficient of a spectral response. Each point estimate in the set of point estimates may correspond to a transformation in the set of transformations. In some embodiments, a linear regression or other normalization technique (e.g., least squares regression) may be performed on the set of point estimates.

At operation 708, the system (e.g., an image processor component of the ultrasound system) may extract a set of attenuation coefficients based on the set of point estimates for the frequency dependent filtering coefficient. In some embodiments, the set of attenuation coefficients is based on a slope of at least one line formed from the set of point estimates.

At operation 710, the system (e.g., an image processor component of the ultrasound system) may generate image data for the material of interest based on the set of attenuation coefficients. In generating the image data, the system may compensate for spectral response reduction of the transducer based on the set of attenuation coefficients and generate an image of the material of interest for display. According to various embodiments, the compensation for spectral response may vary with range, azimuth, or a combination of these or other factors.

In some embodiments, the image data may be generated based on a second pulse signal. For example, the system may transmit a second pulse signal into the tissue, receive a second echo signal corresponding to the second pulse signal, generate second echo data corresponding to the second pulse signal, and generate image data based on the second echo data and the set of attenuation coefficients. The second pulse signal may be imaging pulse signal with a narrower spectrum than the first calibration pulse signal.

Various aspects of the present disclosure relate to a system. The system may include one or more hardware processors configured by machine-readable instructions. The processor(s) may be configured to receive echo data corresponding to a detection of an echo of a pulse signal. The echo data may be associated with a variety of depths of a material of interest. The processor(s) may be configured to generate a set of transformations based on the echo data. Each transformation in the set of transformations may be associated with a depth value. The processor(s) may be configured to generate a set of point estimates for a frequency dependent filtering coefficient of a spectral response. Where each point estimate in the set of point estimates may correspond to a transformation in the set of transformations. The processor(s) may be configured to extract a set of attenuation coefficients based on the set of point estimates for the frequency dependent filtering coefficient. The processor(s) may be configured to generate image data for the material of interest based on the set of attenuation coefficients.

Other aspects of the present disclosure relate to a method. The method may include receiving echo data corresponding to a detection of an echo of a pulse signal. The echo data may be associated with a variety of depths of a material of interest. The method may include generating a set of transformations based on the echo data. Each transformation in the set of transformations may be associated with a depth value. The method may include generating a set of point estimates for a frequency dependent filtering coefficient of a spectral response. Where each point estimate in the set of point estimates may correspond to a transformation in the set of transformations. The method may include extracting a set of attenuation coefficients based on the set of point estimates for the frequency dependent filtering coefficient. The method may include generating image data for the material of interest based on the set of attenuation coefficients.

Yet other aspects of the present disclosure relate to a non-transient computer-readable storage medium having instructions embodied thereon, the instructions being executable by one or more processors to perform a method. The method may include receiving echo data corresponding to a detection of an echo of a pulse signal. The echo data may be associated with a variety of depths of a material of interest. The method may include generating a set of transformations based on the echo data. Each transformation in the set of transformations may be associated with a depth value. The method may include generating a set of point estimates for a frequency dependent filtering coefficient of a spectral response. Where each point estimate in the set of point estimates may correspond to a transformation in the set of transformations. The method may include extracting a set of attenuation coefficients based on the set of point estimates for the frequency dependent filtering coefficient. The method may include generating image data for the material of interest based on the set of attenuation coefficients.

This disclosure has been made with reference to various exemplary embodiments including the best mode. However, those skilled in the art will recognize that changes and modifications may be made to the exemplary embodiments without departing from the scope of the present disclosure. For example, various operational steps, as well as components for carrying out operational steps, may be implemented in alternate ways depending upon the particular application or in consideration of any number of cost functions associated with the operation of the system, e.g., one or more of the steps may be deleted, modified, or combined with other steps.

While the principles of this disclosure have been shown in various embodiments, many modifications of structure, arrangements, proportions, elements, materials, and components, which are particularly adapted for a specific environment and operating requirements, may be used without departing from the principles and scope of this disclosure. These and other changes or modifications are intended to be included within the scope of the present disclosure.

The foregoing specification has been described with reference to various embodiments. However, one of ordinary skill in the art will appreciate that various modifications and changes can be made without departing from the scope of the present disclosure. Accordingly, this disclosure is to be regarded in an illustrative rather than a restrictive sense, and all such modifications are intended to be included within the scope thereof. Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, a required, or an essential feature or element. As used herein, the terms "comprises," "comprising," and any other variation thereof, are intended to cover a non-exclusive inclusion, such that a process, a method, an article, or an apparatus that comprises a list of elements does not include only those elements but may include other elements not expressly listed or inherent to such process, method, system, article, or apparatus. Also, as used herein, the terms "coupled," "coupling," and any other variation thereof are intended to cover a physical connection, an electrical connection, a magnetic connection, an optical connection, a communicative connection, a functional connection, and/or any other connection.

Those having skill in the art will appreciate that many changes may be made to the details of the above-described embodiments without departing from the underlying principles of the invention. The scope of the present invention should, therefore, be determined only by the following claims.

What is claimed is:

1. An ultrasound system comprising:
   a transducer configured to:
      transmit a first pulse signal into a particular tissue of interest, wherein the first pulse signal comprises a known broadband calibration signal having a frequency range greater than pulse signals used for acquiring image data,
      receive a first echo signal corresponding to the first pulse signal, and
      generate echo data based on the first echo signal; and
   an image processor configured to obtain an estimate of depth varying spectral characteristics for the transducer and the particular tissue of interest based on the broadband calibration signal transmitted into the particular tissue of interest by:
      generating a set of fast Fourier transforms based on the echo data, wherein each fast Fourier transform in the set of fast Fourier transforms is associated with one of a plurality of partially overlapping depth ranges in which each adjacent depth range of the plurality of overlapping depth ranges overlaps in at least one point and does not overlap in at least one point, each of the partially overlapping depth ranges including a range of depth values having a minimum depth value and a maximum depth value that are different from those of an adjacent range of depth values,
      generating a set of point estimates for a frequency dependent filtering coefficient of a spectral response, where each point estimate in the set of point estimates corresponds to a fast Fourier transform in the set of fast Fourier transforms at one of the plurality of partially overlapping depth ranges, and
      extract a set of attenuation coefficients based on the set of point estimates for the frequency dependent filtering coefficient;
   wherein the transducer is further configured to:
      transmit a second pulse signal into the particular tissue of interest,
      wherein the second pulse signal is an imaging pulse signal with a narrower frequency range than the first pulse signal,
      receive a second echo signal corresponding to the second pulse signal, and
      generate second echo data corresponding to the second pulse signal,
   wherein the image processor is further configured to use the estimate of depth varying spectral characteristics for the transducer and the particular tissue of interest to improve resolution of image data based on the second echo data by, compensating for spectral response reduction of the transducer, wherein compensating comprises applying one or more depth-dependent inverse filters using the set of attenuation coefficients derived from transmitting the known broadband calibration signal into the particular tissue of interest.

2. The ultrasound system of claim 1, wherein the image processor is further configured to perform a least means square fit on the set of point estimates.

3. The ultrasound system of claim 1, wherein the set of attenuation coefficients is based on a slope of at least one line formed from the set of point estimates.

4. The ultrasound system of claim 1, wherein the compensation for spectral response is varying with range.

5. The ultrasound system of claim 1, wherein the compensation for spectral response is varying in azimuth.

6. The ultrasound system of claim 1, wherein the compensation for spectral response is varying in range and azimuth.

7. A non-transitory computer-readable storage medium having stored therein instructions which, when executed by one or more processors, cause the one or more processors to perform operations comprising:
   transmitting, via a transducer into a particular tissue of interest, a known broadband calibration signal having a frequency range greater than pulse signals used for acquiring image data;
   receiving a calibration echo signal corresponding to the known broadband calibration signal;
   generating calibration echo data based on the known broadband calibration signal;
   obtaining an estimate of depth varying spectral characteristics for the transducer and the particular tissue of interest based on the broadband calibration signal transmitted into the particular tissue of interest by:
      generating a set of fast Fourier transformations based on the calibration echo data, wherein each fast Fourier transformation in the set of fast Fourier transformations is associated with one of a plurality of partially overlapping depth ranges in which each adjacent depth range of the plurality of overlapping depth ranges overlaps in at least one point and does not overlap in at least one point, each of the partially overlapping depth ranges including a range of depth values having a minimum depth value and a maximum depth value that are different from those of an adjacent range of depth values;
      generating a set of point estimates for a frequency dependent filtering coefficient of a spectral response, where each point estimate in the set of point estimates corresponds to a fast Fourier transformation in the set of fast Fourier transformations at one of the plurality of partially overlapping depth ranges; and
      extracting a set of attenuation coefficients based on the set of point estimates for the frequency dependent filtering coefficient;

transmitting an imaging pulse signal into the particular tissue of interest,
wherein the imaging pulse signal has a narrower spectrum than the known broadband calibration signal transmitted into the particular tissue of interest;
receiving an imaging echo signal corresponding to the imaging pulse signal;
and
using the estimate of depth varying spectral characteristics for the transducer and the particular tissue of interest to improve resolution of image data generated from the imaging echo signal by compensating for spectral response reduction based on the set of attenuation coefficients, wherein compensating comprises applying one or more depth-dependent inverse filters using the set of attenuation coefficients derived from the known broadband calibration signal transmitted into the particular tissue of interest.

8. The non-transitory computer-readable storage medium of claim 7, wherein the calibration echo data is associated with a variety of depths for the particular tissue of interest.

9. The non-transitory computer-readable storage medium of claim 7, wherein the set of attenuation coefficients is based on a slope of at least one line formed from the set of point estimates.

10. The ultrasound system of claim 1, wherein image processor coherently averages the echo data of the calibration echo signal over time to improve a signal to noise ratio of an estimated attenuation.

* * * * *